(12) United States Patent
Cohen et al.

(10) Patent No.: US 8,167,813 B2
(45) Date of Patent: May 1, 2012

(54) SYSTEMS AND METHODS FOR LOCATING A BLOOD VESSEL

(75) Inventors: Robert F. Cohen, Kensington, MD (US); David M. Tumey, Germantown, MD (US)

(73) Assignee: Immersion Medical, Inc., Baltimore, MD (US)

( * ) Notice: Subject to any disclaimer, the term of this patent is extended or adjusted under 35 U.S.C. 154(b) by 721 days.

(21) Appl. No.: 11/749,825

(22) Filed: May 17, 2007

(65) Prior Publication Data
US 2008/0287824 A1    Nov. 20, 2008

(51) Int. Cl.
*A61B 5/00*    (2006.01)
(52) U.S. Cl. .................................................. 600/549
(58) Field of Classification Search .................... 600/549
See application file for complete search history.

(56) References Cited

U.S. PATENT DOCUMENTS

| | | |
|---|---|---|
| 3,618,070 A | 11/1971 | Kagan |
| 3,911,416 A | 10/1975 | Feder |
| 4,028,502 A | 6/1977 | Moricca et al. |
| 4,227,319 A | 10/1980 | Guy et al. |
| 4,262,549 A | 4/1981 | Schwellenbach |
| 4,278,920 A | 7/1981 | Ruoff, Jr. |
| 4,333,070 A | 6/1982 | Barnes |
| 4,352,091 A | 9/1982 | Yamasaki |
| 4,421,953 A | 12/1983 | Zielinski |
| 4,436,188 A | 3/1984 | Jones |
| 4,464,117 A | 8/1984 | Foerst |
| 4,484,191 A | 11/1984 | Vavra |
| 4,581,972 A | 4/1986 | Hoshino |
| 4,603,284 A | 7/1986 | Perzley |
| 4,794,392 A | 12/1988 | Selinko |
| 4,823,634 A | 4/1989 | Culver |
| 4,853,674 A | 8/1989 | Kiss |
| 4,918,438 A | 4/1990 | Yamasaki |
| 4,931,765 A | 6/1990 | Rollins et al. |
| 4,964,004 A | 10/1990 | Barker |
| 5,003,984 A | 4/1991 | Muraki et al. |
| 5,117,449 A | 5/1992 | Metroka et al. |
| 5,165,897 A | 11/1992 | Johnson |
| 5,175,459 A | 12/1992 | Danial et al. |

(Continued)

FOREIGN PATENT DOCUMENTS

DE    10 2004 001931    8/2005

(Continued)

OTHER PUBLICATIONS

Patent Cooperation Treaty, International Search Report, International Application No. PCT/US2008/004471, mailed Jul. 18, 2008.

(Continued)

*Primary Examiner* — Max Hindenburg
*Assistant Examiner* — Renee Danega
(74) *Attorney, Agent, or Firm* — Kilpatrick Townsend & Stockton LLP

(57) ABSTRACT

Systems and methods for locating a blood vessel are described. One described method includes receiving a first temperature measure associated with a first point on a surface of a skin; receiving a second temperature measure associated with a second point on the surface of the skin, and determining a differential between the first temperature measure and the second temperature measure. The method further includes generating an output signal indicating the presence of a blood vessel if the differential exceeds a threshold.

41 Claims, 5 Drawing Sheets

U.S. PATENT DOCUMENTS

| | | | |
|---|---|---|---|
| 5,189,389 A | 2/1993 | DeLuca et al. | |
| 5,205,293 A * | 4/1993 | Ito et al. | 600/504 |
| 5,283,970 A | 2/1994 | Aigner | |
| 5,366,376 A | 11/1994 | Copperman et al. | |
| 5,368,484 A | 11/1994 | Copperman et al. | |
| 5,414,337 A | 5/1995 | Schuler | |
| 5,436,622 A | 7/1995 | Gutman et al. | |
| 5,437,607 A | 8/1995 | Taylor | |
| 5,459,382 A | 10/1995 | Jacobus et al. | |
| 5,482,051 A | 1/1996 | Reddy et al. | |
| 5,489,812 A | 2/1996 | Furuhata et al. | |
| 5,506,605 A | 4/1996 | Paley | |
| 5,508,688 A | 4/1996 | Mochizuki | |
| 5,575,761 A | 11/1996 | Hajianpour | |
| 5,619,181 A | 4/1997 | Murray | |
| 5,625,576 A | 4/1997 | Massie et al. | |
| 5,642,413 A | 6/1997 | Little | |
| 5,646,589 A | 7/1997 | Murray et al. | |
| 5,666,473 A | 9/1997 | Wallace | |
| 5,692,956 A | 12/1997 | Rifkin | |
| 5,696,497 A | 12/1997 | Mottier et al. | |
| 5,729,589 A | 3/1998 | Samson | |
| 5,754,096 A | 5/1998 | Muto et al. | |
| 5,757,280 A | 5/1998 | Motohashi | |
| 5,764,751 A | 6/1998 | Konishi | |
| 5,767,787 A | 6/1998 | Kudoh et al. | |
| 5,816,823 A | 10/1998 | Naimark et al. | |
| 5,844,392 A | 12/1998 | Peurach et al. | |
| 5,844,498 A | 12/1998 | Ide | |
| 5,867,796 A | 2/1999 | Inutsuka | |
| 5,873,024 A | 2/1999 | Suzuki | |
| 5,887,995 A | 3/1999 | Holehan | |
| 5,889,670 A | 3/1999 | Schuler et al. | |
| 5,917,906 A | 6/1999 | Thornton | |
| 5,955,964 A | 9/1999 | Tada | |
| 5,956,484 A | 9/1999 | Rosenberg et al. | |
| 5,966,655 A | 10/1999 | Hardouin | |
| 5,973,689 A | 10/1999 | Gallery | |
| 5,988,902 A | 11/1999 | Holehan | |
| 6,014,572 A | 1/2000 | Takahashi | |
| 6,046,726 A | 4/2000 | Keyson | |
| 6,091,321 A | 7/2000 | Karell | |
| 6,113,459 A | 9/2000 | Nammoto | |
| 6,118,979 A | 9/2000 | Powell | |
| 6,131,097 A | 10/2000 | Peurach et al. | |
| 6,175,721 B1 | 1/2001 | Hayato | |
| 6,218,958 B1 | 4/2001 | Eichstaedt et al. | |
| 6,218,966 B1 | 4/2001 | Goodwin et al. | |
| 6,272,319 B1 | 8/2001 | Narusawa | |
| 6,300,938 B1 | 10/2001 | Culver | |
| 6,307,465 B1 | 10/2001 | Kayama et al. | |
| 6,373,463 B1 | 4/2002 | Beeks | |
| 6,374,255 B1 | 4/2002 | Peurach et al. | |
| 6,418,323 B1 | 7/2002 | Bright et al. | |
| 6,424,251 B1 | 7/2002 | Byrne | |
| 6,433,771 B1 | 8/2002 | Yocum et al. | |
| 6,448,977 B1 | 9/2002 | Braun et al. | |
| 6,464,646 B1 * | 10/2002 | Shalom et al. | 600/549 |
| 6,563,487 B2 | 5/2003 | Martin et al. | |
| 6,574,489 B1 | 6/2003 | Uriya | |
| 6,650,338 B1 | 11/2003 | Kolarov et al. | |
| 6,686,901 B2 | 2/2004 | Rosenberg | |
| 6,819,312 B2 | 11/2004 | Fish | |
| 6,864,877 B2 | 3/2005 | Braun et al. | |
| 2002/0145512 A1 | 10/2002 | Sleichter, III et al. | |
| 2002/0149561 A1 | 10/2002 | Fukumoto et al. | |
| 2003/0030619 A1 | 2/2003 | Martin et al. | |
| 2003/0090460 A1 | 5/2003 | Schena et al. | |
| 2003/0122658 A1 | 7/2003 | Takahashi | |
| 2003/0169151 A1 | 9/2003 | Ebling et al. | |
| 2003/0188594 A1 | 10/2003 | Levin et al. | |
| 2003/0222766 A1 | 12/2003 | Rollins et al. | |
| 2004/0014484 A1 | 1/2004 | Kawashima | |
| 2004/0056840 A1 | 3/2004 | Goldenberg et al. | |
| 2004/0152991 A1 | 8/2004 | Pompei | |
| 2005/0065451 A1 * | 3/2005 | Pompei et al. | 600/549 |
| 2005/0093847 A1 | 5/2005 | Altkorn et al. | |
| 2005/0109145 A1 | 5/2005 | Levin et al. | |
| 2005/0162383 A1 | 7/2005 | Rosenberg | |
| 2006/0020212 A1 | 1/2006 | Xu et al. | |
| 2006/0253005 A1 * | 11/2006 | Drinan et al. | 600/300 |

FOREIGN PATENT DOCUMENTS

| | | |
|---|---|---|
| WO | WO 95/20787 | 8/1995 |
| WO | WO 97/18546 | 5/1997 |
| WO | WO 99/48420 | 9/1999 |
| WO | WO 01/91100 | 11/2001 |
| WO | WO 2007/006134 | 1/2007 |

OTHER PUBLICATIONS

Curry, K., Supporting Collaborative Interaction in Tele-immersion, Thesis submitted to the Faculty of the Virginia Polytechnic Institute and the State University in partial fulfillment of the requirements for the degree of Master of Science in Computer Science and Applications, 1998.

Dennerlein, J. et al., Vibrotactile Feedback for Industrial Telemanipulators, Presented at the Sixth Annual Symposium on Haptic Interfaces for Virtual Environment and Teleoperator Systems, ASME IMECE, Dallas, Texas, Nov. 15-21, 199.

Eberhardt, S. et al., Force Reflection for Wimps: A Button Acquisition Experiment, Proceedings of the ASME Dynamic Systems and Control Division, presented at eh 1997 ASME Internaational Mechanical Engineering Congress and Exposition, Nov. 16-21, 1997, Dallas, Texas.

IEEE International Conference on Robotics and Automation, May 16-20, 1998, Lueven, Belgium.

Hayward, V. et al., Parameter Sensitivity Analysis for Design and Control of Force Transmission Systems, McGill University Center for Intelligent machines, 3480 Universtiy Street, Montreal, Quebec.

Kim, W., Telemanipulator Technology and Space Telerobotics, Proceedings from SPIE—The International Society for Optical Engineering, Sep. 7-9, 1993, Boston, Mass.

Kontarinis, D. et al., Tactile Display of Vibratory Information in Teleoperation and Virtual Environments, Presence, vol. 4, No. 4, Fall 1995, pp. 387-402.

Kontarinis, D. et al., Display of High-Frequency Tactile Information to Teleoperators, Harvard University Division of Applied Sciences, Cambridge, Mass.

MacLean, K., Designing with Haptic Feedback, Symposium on Haptic Feedback in the Proceedings of the IEEE Conference on Robotics and Automation, Apr. 22-28, 2000.

Marcus, B., Touch Feedback in Surgery, Official Proceedings of Virtual Reality and Medicine the Cutting Edge, Sep. 8-11, 1994, The New York Hilton.

McAffee, D. et al., Teleoperator Subsystem/ Telerobot Demonstrator: Force Reflecting Hand Controller Equipment Manual, Jet Propulsion Laboratory, Jan. 1988.

McLaughlin, M. et al., The USC Interactive Art Museum: Removing the Barriers between Museums and their Constituencies, web site at http://ascusc.org/icmc/paperforica.html, as available via the Internet and printed Jul. 22, 2003.

Mine, M. et al., Virtual Environment Interaction Techniques, Department of Computer Science, University of North Carolina, Chapel Hill, NC, 1995.

Minsky, M., Computational Haptics: The Sandpaper System for Synthesizing Texture for a Force-Feedback Display, Submitted to the Program in Media Arts and Sciences, School of Architecture and Planning, in partial fulfillment of the requirements for the degree of Doctor of Philosophy at the Massachusetts Institute of Technology, Jun. 1995.

Noll, M., Man-Machine Tactile, SID Journal, Jul./Aug. 1972.

Ouh-Young, M. et al., Creating an Illusion of Feel: Control Issues in Force Display, Computer Science Department, University of North Carolina at Chapel Hill, Sep. 16, 1989.

Ouh-Young, M., Force Display in Molecular Docking, The University of North Carolina at Chapel Hill, 1990.

Ouh-Young, M. et al., The Development of a Low-Cost Force Feedback Joystick and its Use in the Virtual Environment. Proceedings of the Third pacific Conference on Computer Graphics and Applications, Pacific Graphics , Aug. 21-24, 1995.

Pao, L. et al., Synergistic Visual/Haptic Computer Interfaces, Hanoi, Vietnam, pp. 155-162, May 1998.

Patrick, N. et al., Design and Testing of a Non-Reactive, Fingertip, Tactile Display fro Interaction with Remote Environments, Massachusetts Institute of Technology, Department of Mechanical Engineering.

Patrick, N., Design, Construction, and Testing of a Fingertip Tactile Display for Interaction with Virtual and Remote Environments, Submitted to the Department of Mechanical Engineering in partial fulfillment of the requirement for the degree of Masters of Science in Mechanical Engineering at the Mass. University of Technology, Aug. 1990.

Pimentel, K. et al., Virtual Reality through the New Looking Glass, Second Edition, 1995.

Rabinowitz, W. et al., Multidimensional Tactile Displays: Identification of Vibratory Intensity, Frequency, and Contractor Area, Journal of the Acoustical Society of America, vol. 82, No. 4, Oct. 1987.

Ramstein, C., Combining Haptic and Braille Technologies: Design Issues and Pilot Study, Second Annual ACM Conference on Assistive Technology, Apr. 11-12, 1996.

Rosenburg, L., Virtual Fixtures: Perceptual Overlays Enhance Operator Performance in Telepresence Tasks, A Dissertation submitted to the Department of Mechanical Engineering and the Committee on Graduate Studies of Stanford University in partial fulfillment of the requirements for the degree of Doctor of Philosophy, Jun. 1994.

Ruspini, D. et al., The Haptic Display of Complex Graphical Environments, Computer graphics Proceedings, Annual Conference Series, 1997.

Russo, M., The Design and Implementation of a Three Degree of Freedom Force Output Joystick, Submitted to the Department of Mechanical Engineering in partial fulfillment of the requirement for the degree of Masters of Science in Mechanical Engineering at the Mass. University of Technology, May 1990.

Safe Flight Instrument Corporation, Coaxial Control Shaker, part No. C-25502, Jul. 1, 1967, revised Jan. 28, 2002.

Scannell, T., Taking a Joystick Ride, Computer Currents, Boston Edition, vol. 9, No. 11, Nov. 1994.

Schena, B., Patent Application Transmittal, Directional Inertial Tactile Feedback using Rotating Masses, Sep. 28, 2001.

Schmult, B. et al., Application Areas for a Force-Feedback Joystick, DSC-vol. 49, Advances in Robotics, Mechatronics, and Haptic Interfaces, ASME 1993.

Shimoga, K., Finger Force and Touch Feedback Issues in Dexterous Telemanipulation, Proceedings from the Fourth Annual Conference on Intelligent Robotic Systems fro Space Exploration, Rensselaer Plytechnic Institute, Troy, New York, Sep. 30-Oct. 1, 1992.

Snow, E. New Technology Transmittal, Model-X Force Reflecting Hand Controller, Jun. 15, 1989.

SMK, Multi-Functional Touch panel, Force-Feedback Type, Developed, Sep. 30, 2002.

SMK, Force Feedback Type Optical Touch Panel Developed, Oct. 30, 2002.

Stanley, M. et al., Computer Simulation of Interacting Dynamic Mechanical Systems using Distributed Memory Parallel Processors, DSC-vol. 42, Advances in Robotics, ASME 1992.

Terry, J. et al., Tactile Feedback in a Computer Mouse, Proceedings of the Fourteenth Annual Northeast Bioengineering Conference, Mar. 10-11, 1988, University of New Hampshire.

Wiker, S., Teletouch Display Development : Phase 1 Report, Technical Report 1230, Jul. 1988.

Patent Cooperation Treaty, Notification concerning Transmittal of International Preliminary Report on Patentability, International Application No. PCT/US2008/004471, mailed Nov. 26, 2009.

* cited by examiner

SYSTEMS AND METHODS FOR LOCATING A BLOOD VESSEL

FIELD OF THE INVENTION

The present invention generally relates to medical care. More particularly, the present invention relates to systems and methods for locating a blood vessel.

BACKGROUND

Determining the location of a blood vessel is a common medical procedure. Historically however, the systems and methods that medical practitioners use for locating blood vessels have been imprecise, cumbersome, and/or expensive.

For example, one common conventional method for locating a blood vessel involves restricting blood flow to a patient's arm and visually identifying a blood vessel. While this conventional method is widely used and inexpensive, it suffers from several problems. For instance, even in ideal conditions, determining the precise location of a blood vessel using this method may be difficult. Also, the conventional method is invasive, causing a patient discomfort as their arm is being restricted. The procedure may be further complicated with patients who are experiencing trauma, or with patients who have darker or thicker skin.

Rather than using a conventional manual method, a medical practitioner may use a device for locating a blood vessel. However, conventional devices that attempt to locate blood vessels may suffer from inaccuracy, invasiveness, high cost, and relative impracticality. And some devices may only work on certain patients.

Thus a need exists for an accurate, convenient, and inexpensive device for locating blood vessels.

SUMMARY

Embodiments of the present invention disclosed herein provide systems and methods for locating a blood vessel.

One embodiment of the invention is a system comprising a temperature sensor operable to take at least two temperature measures of at least two points on a surface of a skin. The embodiment further comprises a processor in communication with the temperature sensor and configured to receive a first temperature measure from the temperature sensor, receive a second temperature measure from the temperature sensor, determine a differential between the first temperature measure and the second temperature measure, and generate an output signal indicating the presence of a blood vessel if the differential exceeds a threshold. The embodiment may further comprise an indicator configured to receive the output signal and, in response, indicate the presence of the blood vessel.

Another embodiment of the invention implements a method comprising receiving a first temperature measure associated with a first point on a surface of a skin, receiving a second temperature measure associated with a second point on the surface of the skin, and determining a differential between the first temperature measure and the second temperature measure. The method further comprises generating an output signal indicating the presence of a blood vessel if the differential exceeds a threshold. In another embodiment, a computer-readable medium (such as, for example random access memory or a computer disk) comprises code for carrying out such a method.

Further details and advantages of embodiments of the invention are set forth below.

BRIEF DESCRIPTION OF THE DRAWINGS

These and other features, aspects, and advantages of the invention are better understood when the following Detailed Description is read with reference to the accompanying drawings, wherein.

DETAILED DESCRIPTION

Embodiments of the present invention provide systems and methods for locating a blood vessel. In one illustrative embodiment, a blood vessel locator is embodied in a handheld device that includes a temperature sensor. A medical practitioner holds the blood vessel locator on or near the patient's skin, for example, on the skin of the patient's arm. As the medical practitioner moves the locator across the patient's arm, the temperature sensor takes temperature readings at points on the surface of the skin and outputs these temperature readings to a processor housed in the device. Since the temperature of the skin above a blood vessel may be different from the temperature of skin below which no blood vessel is present, a blood vessel may be located by locating a temperature differential between two points on the surface of a skin. The processor continually calculates the differences in skin temperature between the current reading and the previous reading or readings.

When the processor determines that a difference in temperature exists, the processor compares the observed difference between two temperature readings to a pre-determined threshold stored in memory. If the difference exceeds the pre-determined threshold, a blood vessel may be present, and the device provides an indication that a blood vessel has been located. For instance, the device may light a light emitting diode (LED), vibrate the housing, beep, or provide some other indication. The device may also mark the skin with a small ink dot at the location of a blood vessel so the medical practitioner can easily find the spot after the locator has been moved away in preparation for inserting a needle into the blood vessel or performing some other procedure.

This example is given to introduce the reader to the general subject matter discussed. The invention is not limited to this example. Below, an illustrative blood vessel locator is introduced. Then, example blood vessel locators and methods to locate a blood vessel are described.

Illustrative Blood Vessel Locator

Figure 1:
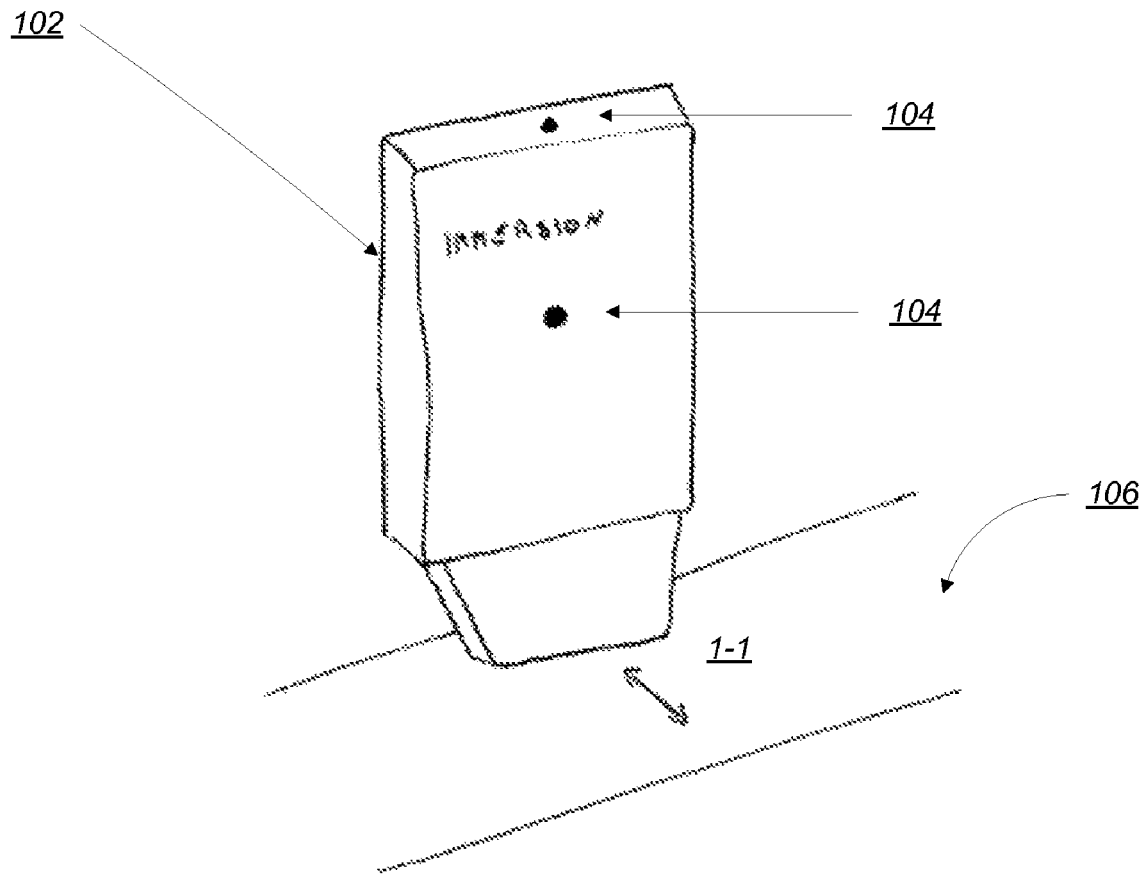
FIG. 1 is an illustration of a blood vessel locator in one embodiment of the present invention.

Referring now to the drawings in which like numerals indicate like elements throughout the several figures, FIG. 1 is an illustration of a blood vessel locator in one embodiment of the present invention.

In one embodiment, the blood vessel locator 102 shown in FIG. 1 is a self-contained, battery-powered handheld device. In other embodiments, the device may be tethered, for instance, to a power supply, visual display, or other device. The locator 102 shown in FIG. 1 is placed above or on the skin of a patient's arm 106. A medical practitioner then guides the locator 102 across the surface of the patient's skin 106. For example, the blood vessel locator 102 may be moved laterally in the direction of arrow 1-1 across the surface of the skin 106.

In other embodiments, the blood vessel locator 102 may be moved in other directions. For instance, the locator 102 may be moved in a circular pattern or laterally and then longitudinally. In other embodiments, the surface of the skin 106 may be moved under the blood vessel locator 102, while the locator 102 remains in a stationary position. For instance, the locator 102 may be fixed in a stand (not shown). While the embodiment shown in FIG. 1 is intended for manual operation, in some embodiments, the blood vessel locator 102 may be operated by mechanical means.

The blood vessel locator 102 also includes one or more temperature sensor(s) (not shown), which are at least partially contained within the housing. As the blood vessel locator 102 moves across the surface of the skin 106, the temperature sensor(s) detect the temperature of the surface of the skin 106. The temperature sensor(s) may be sensitive to a limited range of temperatures. The temperature sensor(s) may provide continuous temperature data when sensing temperatures within this range. The temperature sensor(s) may be located so that the actual sensor passes through an opening on the bottom surface of the housing of the locator 102, and may detect the temperature of the surface of the skin through direct contact. Alternatively, the sensor(s) may be attached to the outside of the housing. Some embodiments utilize one or more temperature sensor(s) that are configured to sense the temperature of the skin without direct contact.

The blood vessel locator 102 shown in FIG. 1 also comprises a processor (not shown). In a handheld device, such as the one illustrated, the processor is contained within the housing of the locator 102. In other embodiments the processor may be positioned externally, for instance, in a host device to which the locator 102 is attached. When the temperature sensor detects a temperature, it outputs the temperature measure to the processor, which stores the temperature measure in some type of computer-readable medium, such as random access memory (RAM).

In one embodiment, once the processor receives at least two temperature measures, it calculates a differential between the two measures. The processor may be programmed to ignore temperature measures within a range of the first temperature measure but may calculate a differential of measures. If the processor determines that the temperature differential indicates the presence of a blood vessel, the blood vessel locator 102 provides some indication that a blood vessel is present. For instance, the blood vessel locator 102 shown in FIG. 1 comprises a light emitting diode (LED) 104 that can be seen by a user of the locator 102. If the processor determines that a blood vessel is present, the processor sends an output signal that causes the LED 104 to light. In some embodiments, the blood vessel locator 102 includes multiple visual indicators, such as several LEDs. In one such embodiment, the LEDs are lit in a pattern simulating a stud-finder, such that a medical practitioner may accurately determine the location of a blood vessel by moving the locator 102 back and forth over the location of a blood vessel while watching the LEDs alternately turn on and off.

In other embodiments, the blood vessel locator 102 may activate other types of indicators or a combination of types of indicators to indicate the presence of a blood vessel. For example, in one embodiment, the blood vessel locator 102 comprises an actuator, such as an eccentric rotating mass (ERM) motor, for outputting haptic effects to a user of the locator 102. Such a device may vibrate when a blood vessel is located or vibrate at an increasing frequency as a blood vessel is approached and a decreasing frequency as the locator 102 moves away from the blood vessel.

Another embodiment comprises a speaker contained within the blood vessel locator 102. The speaker provides an audio cue as to the presence of a blood vessel. In one alternate embodiment of the present invention, the blood vessel locator 102 comprises a liquid crystal diode (LCD) display, configured to provide a thermal picture of the surface of the skin 106 and thereby indicate the location or locations of blood vessels.

Locator Having One Temperature Sensor and One Indicator

Figure 2:
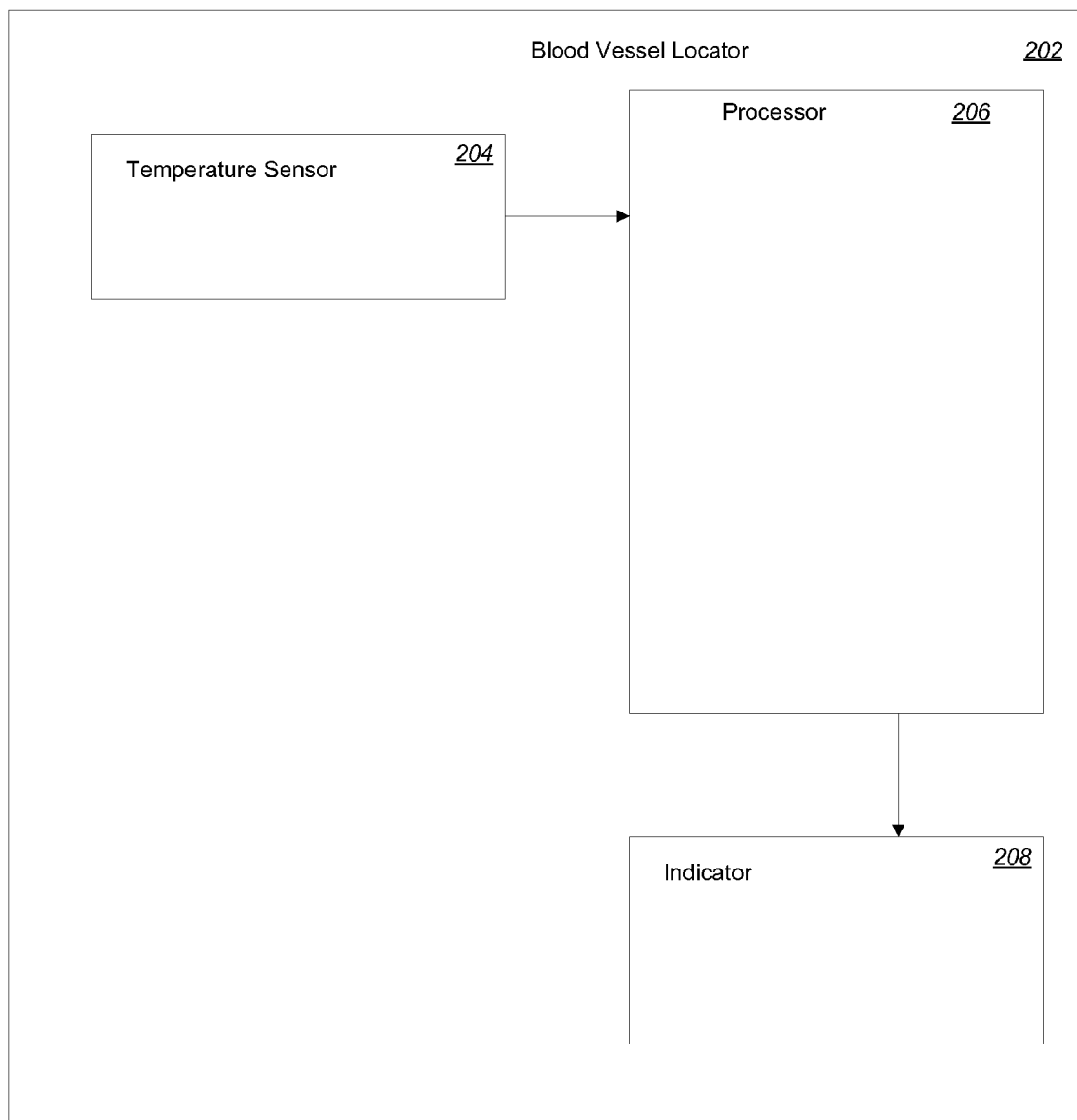
FIG. 2 is a block diagram illustrating a blood vessel locator in one embodiment of the present invention.

FIG. 2 is a block diagram illustrating a blood vessel locator in one embodiment of the present invention In the embodiment shown, the blood vessel locator 202 comprises one temperature sensor 204. In other embodiments, the locator may comprise two, three, or more temperature sensors. The temperature sensor 204 is operable to measure the temperature of a point on the surface of the skin and output the temperature measure. While much of the description contained herein references a human's skin, embodiments of the present invention are not limited to use on a human's skin and may be used, for instance, to locate blood vessels in various other animals, such as other primates, dogs, and cats. In some instances, for animals, the fur may have to be shaved prior to measuring skin temperatures.

The temperature sensor 204 may utilize any of a number of different temperature measuring technologies. For example, the temperature sensor 204 may comprise a thermocouple contact sensor. In such embodiments, the temperature sensor 204 may detect the temperature of the surface of the skin through direct contact with the skin. In other embodiments of the invention, the temperature sensor 204 may be a different type of temperature sensor. For example, the temperature sensor 204 may be an infrared thermometer, capable of detecting the temperature of the skin without direct skin contact.

In embodiments of the invention requiring direct contact with the skin for temperature measurement, the blood vessel locator 202 may comprise an additional disposable component. For example, the disposable component may comprise a sterile plastic sleeve, capable of covering the temperature sensor 204. The additional disposable component may help to ensure good hygiene and may also help to shield the device from contamination.

While detection of blood vessels using embodiments of the present invention may be possible without any preparation, temperature differentials may in some circumstances be more easily detected by the temperature sensor 204 if the surface of the skin is warmed or cooled before the temperature measure is taken. For example, a practitioner may warm a patient's arm by soaking it with warm water before using the blood vessel locator 202.

Referring still to FIG. 2, the blood vessel locator 202 shown also comprises a processor 206. The processor 206 is in communication with the temperature sensor 204 to receive temperature measures.

The processor 206 may comprise a computer-readable medium, such as a random access memory (RAM) (not shown) coupled to the processor. The processor 206 may execute computer-executable program instructions stored in memory. Such processors can include one or more microprocessors, ASICs, and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors include, or can be in communication with, media, for example, which stores instructions that, when executed by the processor, cause the processor to perform the steps described herein. Embodiments of computer-readable media include, but are not limited to, an electronic, optical, magnetic, or other storage or transmission device capable of providing a processor with computer-readable instructions. Other examples of suitable media include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media can transmit or carry instructions to a computer, including a router, private or public network, or other transmission device or channel, both wired and wireless. The instructions can comprise code from any suitable computer-programming language, including, for example, C, C+, C++, Visual Basic, Java, Python, and JavaScript.

The processor 206 may be configured to receive multiple temperature measures from a temperature sensor 204. In other embodiments, the processor 206 may be configured to receive one or more temperature measures from multiple temperature sensors. In the embodiment shown in FIG. 2, the temperature sensor 204 and the processor 206 are in communication via a direct wired digital connection. In other embodiments, communication between a temperature sensor 204 and the processor 206 may be through analog signals and may be wireless. For instance, the temperature sensor 204 may be able to use Bluetooth or Wi-Fi to communicate with the processor 206.

When the processor 206 receives the temperature measure from the temperature sensor 204, the processor 206 may compare the measure to a previously-received temperature measure or to some other data stored in memory (not shown). For instance, the processor 206 may be configured to determine a differential between a first temperature measure and a second temperature measure. The processor 206 may be further configured to determine a differential between a second temperature measure and a third temperature measure. In other embodiments, the processor 206 may instead store a reference or calibration temperature measure and compare temperature measures received from the temperature sensor 204 to the reference or calibration temperature measure.

Once the processor has determined the differential, the processor 206 may compare the differential to a threshold. If the differential meets or exceeds the threshold, then the processor 206 may be configured to generate an output signal indicating the presence of a blood vessel.

In some embodiments, if the processor 206 determines that a differential between two temperature measures or between a temperature measure and a calibration or reference measure exceeds a threshold, the processor 206 generates an output signal. The threshold, for example, may be any differential amount that is indicative of the presence of a blood vessel. For instance, in one embodiment, the threshold is set at 0.5 degrees Fahrenheit. The differential may be predetermined as in the example described, or a medical practitioner may configure the differential threshold during operation of the blood vessel locator 202 to account for variations in patients or environments.

Also, in some embodiments, if the processor 206 determines that a differential between two temperature measures does not exceed a threshold, the processor 206 does not generate an output signal. In other embodiments, if the processor 206 determines a differential between two temperature measures does not exceed a threshold, the processor 206 generates a signal indicating the absence of a blood vessel.

In some embodiments, the processor 206 may determine a direction or axis of a blood vessel. Two or more differentials exceeding the threshold may indicate the direction of the blood vessel. For example, a sequence or succession of differentials in excess of a threshold may indicate the direction of a blood vessel. When a direction of a blood vessel is determined, the processor 206 may generate an output signal indicating the direction.

The blood vessel locating device 202 shown in FIG. 2 also comprises an indicator 208. The indicator 208 is configured to receive the output signal from the processor 206. In other embodiments of the blood vessel locating device 202, the device may comprise other types of indicators and may comprise various combinations of multiple indicators.

In some embodiments, the indicator 208 may comprise a visual indicator. Visual indicators may include one or more lights, or a LCD display. For example, the indicator 208 may comprise a single red LED. When the indicator 208 receives a signal from the processor 206 indicating the presence of a blood vessel, the red LED will be activated.

The indicator 208 may also comprise an audio indicator, for example, a speaker. In such embodiments, the indicator 208 may emit a tone when it receives a signal from the processor 206 indicating the presence of a blood vessel.

In some embodiments of the present invention, the blood vessel locator 202 may comprise a marker (not shown). In one such embodiment, the marker is configured to generate a mark on the surface of the skin over the located blood vessel by, for instance, spraying one or more drops of ink on the skin. Multiple drops may indicate the direction or axis of the blood vessel. Then, when the medical practitioner moves the blood vessel locator 202 away from the skin in order to perform a medical procedure, the mark or marks are visible on the skin.

In another embodiment, the marker comprises a light. In one example, the marker may be configured to illuminate the location of the blood vessel on the surface of the skin with a small beam of light. In another example, the light may indicate the direction or axis of the blood vessel. In yet another embodiment, the marker is configured to leave one or more small, temporary indentations on the surface of the skin where the blood vessel is located.

The blood vessel locator 202 may include additional features to enhance its convenience for practitioners. For example, in some embodiments of the blood vessel locator 202, the marker may be used as a flashlight.

In other embodiments, the blood vessel locating device 202 may include a guide for directing medical devices to the located blood vessel. For example, the blood vessel locating device 202 may comprise a slot (not shown) in which or through which an intravenous needle can be directed. The slot is configured so that it directs the needle to the location of the blood vessel as indicated by the blood vessel locator 202. These additional features are illustrative and not exhaustive; other features may also be incorporated into various embodiments of the present invention.

Locator Having Multiple Temperature Sensors and Multiple Indicators

Figure 3:
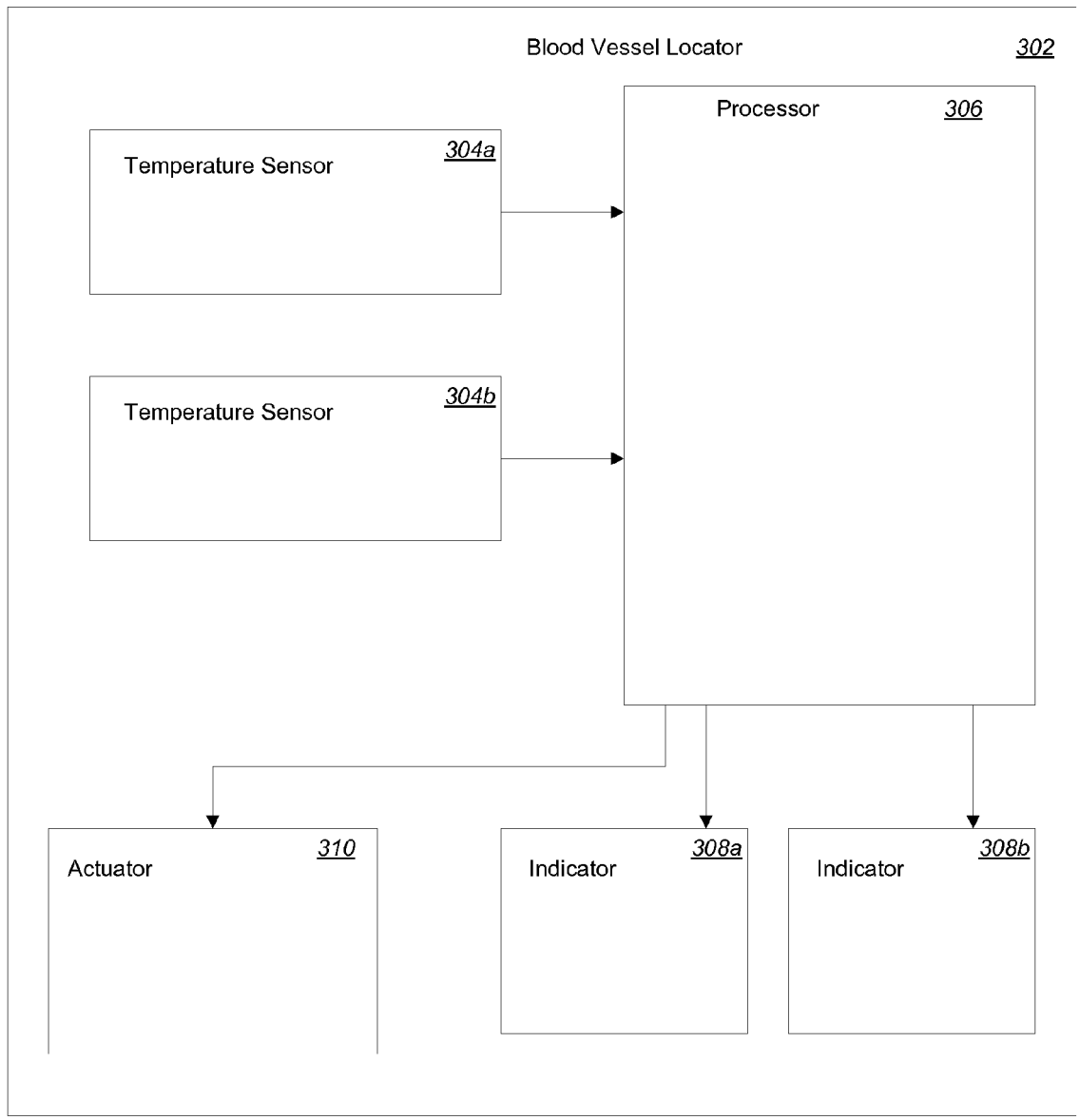
FIG. 3 is a block diagram illustrating a second blood vessel locator in one embodiment of the present invention.

FIG. 3 is a block diagram illustrating a second blood vessel locator in one embodiment of the present invention. The blood vessel locator 302 shown in FIG. 3 comprises two temperature sensors, 304a and 304b. Other embodiments of the blood vessel locator 302 may comprise one, three, or more than three temperature sensors.

The two or more temperature sensors 304 of the blood vessel locator 302 may be configured to detect and output temperature measures substantially simultaneously. For example, each temperature sensor 304a and 304b may be activated at the same time. In other embodiments, the temperature sensors 304 may output temperature measures at different times.

In embodiments of the invention with multiple temperature sensors 304, the sensors may be substantially aligned. For example, in an embodiment comprising three or more temperature sensors, some or all of the temperature sensors may be placed in a linear arrangement. In such embodiments, the temperature sensors 304 may be configured to output temperature measures from adjacent surfaces of the skin. As such, the three temperature measures may originate from three points in a linear alignment on the surface of the skin. Such embodiments may provide faster detection of a blood vessel than an embodiment using fewer sensors.

In other embodiments of the invention with multiple temperature sensors, the temperature sensors may be arranged in an array. The array of temperature sensors may then be capable of capturing a thermal picture of an area of a patient's skin. In areas where the temperature differential exceeds a threshold, the thermal picture may then be used to locate the presence of a blood vessel within the boundary of the picture.

The location of the temperature sensors 304 may be impacted by the type of patient on which the blood vessel locator 302 is to be used. For instance, in order to locate the blood vessels of a child, the temperature sensors 304a and 304b may be aligned more closely together than they would be to locate the blood vessels of an adult. For example, the temperature sensors may be aligned closely together such that each sensor may simultaneously contact the surface of a smaller arm.

The location of the temperature sensors 304 may be fixed in the device. In other embodiments of the invention with multiple temperature sensors, a medical practitioner may manipulate the configuration of the temperature sensors to accommodate individual patients.

In some embodiments of the present invention, the blood vessel locator 302 comprises two or more indicators, such as indicators 308a and 308b shown in FIG. 3. The indicators 308 may be of the same type or of different types. For instance, in one embodiment, indicator 308a may be an LED, while indicator 308b may be a speaker. In such embodiments, the blood vessel locating device 302 may indicate the presence of a blood vessel by simultaneously flashing the LED and emitting a sound through the speaker. In other embodiments, the blood vessel locating device may have different combinations of one or more indicators.

In some embodiments, the blood vessel locating device 302 also comprises an actuator 310. The actuator 310 is configured to provide a haptic effect, such as a vibrotactile effect to a user of the blood vessel locator 302. Further embodiments of the blood vessel locator 302 may comprise a plurality of actuators.

The actuator 310 may be configured to receive the output signal from the processor 306 and provide a haptic effect in response to the output signal. In some embodiments the haptic effect comprises a vibrotactile effect. For example, the actuator 310 may vibrate the housing of the blood vessel locator 302 in response to an output signal indicating the presence of a blood vessel. The actuator 310 may comprise any number of commercially available actuators, such as eccentric rotating mass (ERM) motors, voice coils, linear actuators, moving magnet actuators, piezoelectric actuators, pneumatic actuators, etc.

FIRST EXAMPLE OF A METHOD TO LOCATE A BLOOD VESSEL

Figure 4:
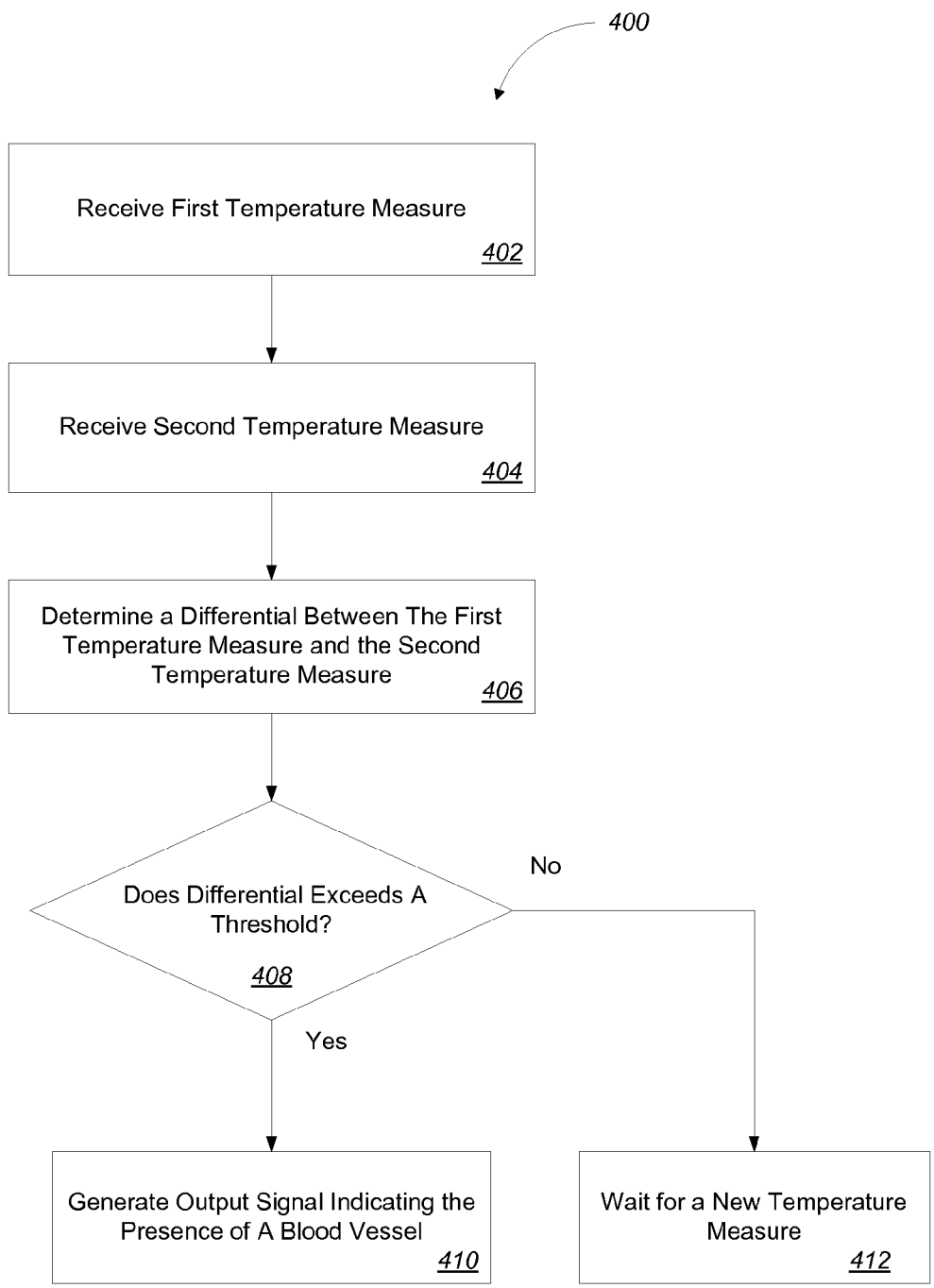
FIG. 4 is a flow diagram illustrating a first method for locating a blood vessel in one embodiment of the present invention.

FIG. 4 is a flow diagram illustrating a first method 400 for locating a blood vessel in one embodiment of the present invention. In step 402, a first temperature measure is received by a processor from a temperature sensor. The temperature measure may comprise a temperature measure on any suitable scale, such as a Fahrenheit or a Celsius temperature measure. In some embodiments of the invention, the temperature measure may be any unit which is proportional to the temperature of the skin, such as, for example, millivolts. The temperature measure may correspond with the temperature of a point on the surface or above the surface of an area of skin. Temperature measures may originate from a human or other animal.

In step 404, a second temperature measure is received by the processor from a temperature sensor. In some embodiments of the invention, a processor can receive the first temperature measure 402 and the second temperature measure 404 as a digital signal. In one embodiment, the first temperature measure and the second temperature measure are received from the same temperature sensor. In other embodiments, the first temperature measure and the second temperature measure may be received from different temperature sensors. Further, in some such embodiments, step 402 and step 404 may occur substantially simultaneously.

In step 406, the processor determines a differential between the first temperature measure and the second temperature measure. For example, if the first temperature measure is 97.0 degrees Fahrenheit, and the second temperature measure is 97.7 degrees Fahrenheit, the temperature differential is 0.7 degrees Fahrenheit. In other embodiments, a processor may determine the differential between the second temperature measure and the third temperature measure.

In step 408, the processor determines whether a blood vessel is present by comparing the differential with a threshold. In some embodiments, the threshold value may be predefined. In other embodiments, the threshold may be specified by a medical practitioner or determined during a calibration process.

If the differential exceeds the threshold, the processor generates an output signal 410. For example, the threshold may be 0.3 degrees Fahrenheit. If the temperature differential between the first temperature measure and the second temperature measure is 0.4 degrees Fahrenheit, then the processor determines that a blood vessel is present and generates an output signal 410. The processor may send the output signal to one or more indicators, including, for example, visual, auditory, and haptic indicators.

In the embodiment of FIG. 4, the processor does not generate an output signal if the presence of a blood vessel is not detected. For example, if the threshold is 3 degrees Fahrenheit, but the differential is 2 degrees Fahrenheit, no output signal is generated. In the process shown in FIG. 4, if the temperature differential does not exceed the threshold, the processor waits for a new temperature measure 412.

SECOND EXAMPLE OF A METHOD TO LOCATE A BLOOD VESSEL

Figure 5:
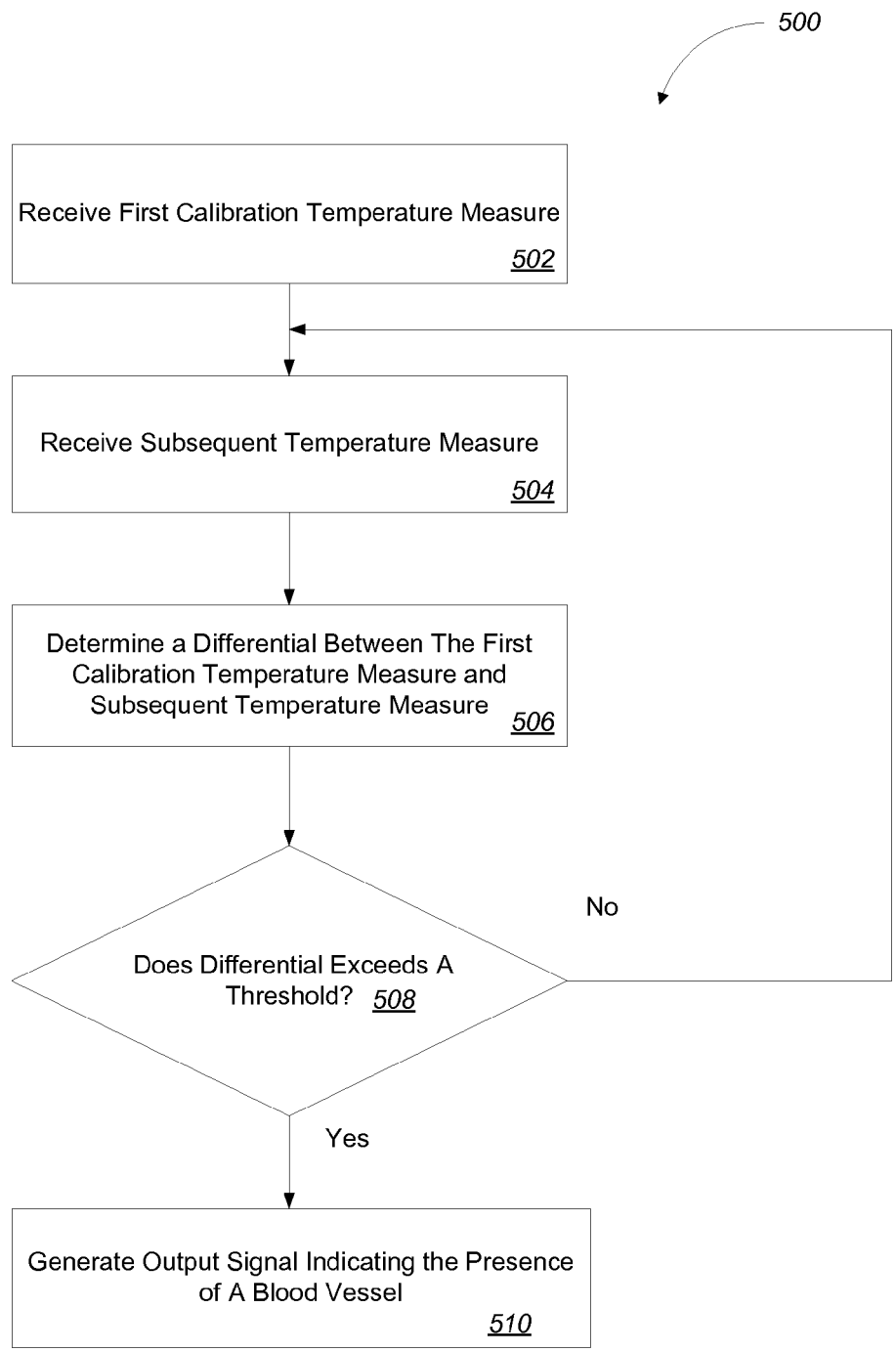
FIG. 5 is a flow diagram illustrating a second method for locating a blood vessel in one embodiment of the present invention.

FIG. 5 is a flow diagram illustrating a second method 500 for locating a blood vessel in one embodiment of the present invention. In step 502, a first calibration temperature measure is received by a processor from a temperature sensor. In some embodiments, the calibration temperature measure is stored by the processor, and compared against successive temperature measures received by the processor. The calibration temperature measure may comprise a temperature measure on any suitable scale, such as a Fahrenheit or a Celsius temperature measure. The calibration temperature measure may correspond with the temperature of a point on the surface or above the surface of an area of skin. Calibration temperature measures may originate from a human or other animal.

In step 504, a subsequent temperature measure is received by a processor from a temperature sensor. In one embodiment, the subsequent temperature measure is from a point on the surface of the skin adjacent to the first calibration temperature measure. In other embodiments, the subsequent temperature measure may be from a point located nonadjacent to the first calibration point.

In step 506, the processor determines a differential between the first calibration temperature measure and the subsequent temperature measure.

In step 508, the processor determines whether a blood vessel is present by comparing the differential between the temperature measures with a threshold. In some embodiments, the threshold value may be predefined. In other embodiments, the threshold may be specified by a medical practitioner or determined during a calibration process.

If the differential exceeds the threshold, the processor generates an output signal 510. The processor may output this signal to one or more indicators, including, for example, visual, auditory, and haptic indicators.

If the differential does not exceed a threshold, the process shown continues by receiving a new subsequent temperature measure 504. The new subsequent temperature measure may originate from a third point on the surface of the skin. The processor then determines a new differential between the calibration temperature measure and the new subsequent temperature measure 506. If the processor determines the new differential exceeds a threshold 508, the processor will generate an output signal indicating the presence of a blood vessel 510.

Embodiments of the present invention provide various advantages over conventional systems and methods for locating blood vessels. For instance some embodiments allow medical practitioners to identify blood vessels in patients having varying skin tones and skin thickness, a task that may be difficult with conventional systems and methods. Further, some embodiments of the present invention are substantially less expensive than conventional devices for locating blood vessels. And embodiments of the present invention may be easier to use and less invasive, facilitating a higher level of care from the medical practitioner and less trauma for the patient.

GENERAL

The foregoing description of embodiments of the invention has been presented only for the purpose of illustration and description and is not intended to be exhaustive or to limit the invention to the precise forms disclosed. Numerous modifications and adaptations thereof will be apparent to those skilled in the art without departing from the spirit and scope of the present invention.

That which is claimed:

1. A handheld system for locating a blood vessel, the system comprising:
    a housing configured to be moved across a patient's skin;
    a temperature sensor disposed within the housing and operable to output a temperature measure of a location on a surface of the patient's skin; and
    a processor in communication with the temperature sensor and configured to:
        receive a first temperature measure at a first location from the temperature sensor,
        receive a second temperature measure at a second location from the temperature sensor, the second location different from the first location,
        determine a difference between the first temperature measure and the second temperature measure, and
        generate an output signal indicating the presence of a blood vessel if the difference exceeds a threshold,
    wherein the temperature sensor is configured to output the first and second temperature measures at the first and second locations based on a movement of the housing across the patient's skin.

2. The system of claim 1, further comprising an indicator configured to receive the output signal and indicate the presence of the blood vessel.

3. The system of claim 1, wherein the processor is further configured to determine a direction of the blood vessel.

4. The system of claim 3, wherein the indicator is further configured to indicate the direction of the blood vessel.

5. The system of claim 2, wherein the indicator comprises a visual indicator.

6. The system of claim 2, wherein the indicator comprises an audible indicator.

7. The system of claim 2, wherein the indicator comprises a marker configured to generate a mark on the surface of the skin over the blood vessel.

8. The system of claim 1, further comprising an actuator configured to provide a haptic effect in response to the output signal.

9. The system of claim 8, wherein the haptic effect comprises a vibrotactile haptic effect.

10. A handheld system for locating a blood vessel, the system comprising:
    a housing configured to be moved across a patient's skin;
    a first temperature sensor disposed within the housing and operable to output a temperature measure of a first location on a surface of a skin;
    a second temperature sensor disposed within the housing and operable to output a second temperature measure of a second location on the surface of the skin; and
    a processor in communication with the first temperature sensor and the second temperature sensor, the processor configured to:
        receive the first temperature measure from the first temperature sensor,
        receive the second temperature measure from the second temperature sensor,
        determine a difference between the first temperature measure and the second temperature measure, and
        generate a first output signal indicating the presence of a blood vessel if the difference exceeds a threshold.

11. The system of claim 10, further comprising an indicator configured to receive the first output signal and indicate the presence of the blood vessel.

12. The system of claim 11, further comprising:
a third temperature sensor in communication with the processor, the third temperature sensor operable to output a third temperature measure of a third point on the surface of the skin;
and wherein the processor is further configured to:
receive the third temperature measure from the third temperature sensor;
determine a second difference between the second temperature measure and the third temperature measure,
generate a second output signal indicating the presence of a blood vessel if the second difference exceeds a threshold; and
the indicator further configured to receive the second output signal and indicate the presence of the blood vessel.

13. The system of claim 12, wherein the first temperature sensor, the second temperature sensor, and the third temperature sensor are substantially aligned.

14. A handheld system for locating a blood vessel, the system comprising:
a plurality of temperature sensors, each operable to output a temperature measure of a point on the surface of a skin; and
a processor in communication with the plurality of temperature sensors, the processor configured to:
receive the temperature measure from each of the plurality of temperature sensors,
determine a difference between any of two of the temperature measures, and
generate an output signal indicating the presence of a blood vessel if the difference exceeds a threshold.

15. The system of claim 14, further comprising an indicator configured to receive the output signal and indicate the presence of the blood vessel.

16. The system of claim 14, wherein the plurality of temperature sensors are substantially aligned.

17. The system of claim 14, wherein the plurality of temperature sensors are arranged as an array.

18. A method for locating a blood vessel with a handheld device, the method comprising:
receiving a first temperature measure associated with a first location on a surface of a skin, the first temperature measure generated by a temperature sensor;
moving the temperature sensor to a second location;
receiving a second temperature measure associated with the second location on the surface of the skin, the second temperature measure generated by the temperature sensor;
determining a difference between the first temperature measure and the second temperature measure; and
generating an output signal indicating the presence of a blood vessel if the difference exceeds a threshold.

19. The method of claim 18, further comprising receiving the output signal and signaling the presence of a blood vessel.

20. The method of claim 18, further comprising determining a direction of a blood vessel.

21. The method of claim 18, further comprising:
receiving a third temperature measure associated with a third point on a surface of the skin;
determining a second difference between the second temperature measure and the third temperature measure; and
generating an output signal indicating the presence of a blood vessel if the second difference exceeds a threshold.

22. The method of claim 18, wherein the first temperature measure is a calibration temperature measure.

23. The method of claim 18, further comprising identifying the location of the blood vessel on the surface of the skin.

24. The method of claim 23, wherein identifying the location of the blood vessel on the surface of the skin comprises generating a mark on the surface of the skin.

25. The method of claim 20, further comprising identifying the direction of the blood vessel on the surface of the skin.

26. The method of claim 18, wherein the first temperature measure and the second temperature measure are received from a single sensor.

27. The method of claim 18, wherein the first temperature measure is received from a first sensor and the second temperature measure is received from a second sensor.

28. The method of claim 27, wherein:
the first sensor is in contact with a first point on the surface of the skin; and
the second sensor is in contact with a second point on the surface of the skin.

29. The method of claim 18, wherein receiving the first temperature measure and the second temperature measure occur substantially simultaneously.

30. The method of claim 19, wherein signaling the presence of a blood vessel comprises generating a visual effect.

31. The method of claim 19, wherein signaling the presence of a blood vessel comprises generating an auditory effect.

32. The method of claim 19, wherein signaling the presence of a blood vessel comprises generating a haptic effect.

33. The method of claim 32, wherein the haptic effect comprises a vibrotactile haptic effect.

34. The method of claim 19, wherein signaling the presence of a blood vessel comprises generating a plurality of sensory effects.

35. A method for locating a blood vessel with a handheld device, the method comprising:
receiving a plurality of temperature measures from a temperature sensor being moved across a patient's skin, each of the plurality of temperature measures associated with a different location on a surface of the patient's skin;
determining a difference between a pair of the plurality of temperature measures; and
generating an output signal indicating the presence of a blood vessel if the difference exceeds a threshold.

36. A non-transitory computer-readable medium on which is encoded computer-executable program code, the program code comprising:
program code for receiving a first temperature measure associated with a first location on a surface of a skin, the first temperature measure generated by a temperature sensor disposed within a housing of a handheld device;
program code for receiving a second temperature measure associated with a second location on the surface of the skin, the second temperature measure generated by the temperature sensor;
program code for determining a difference between the first temperature measure and the second temperature measure; and
program code for generating an output signal indicating the presence of a blood vessel if the difference exceeds a threshold, wherein the temperature sensor is configured to output the first and second temperature measures at the first and second locations based on a movement of the housing across the patient's skin.

37. The non-transitory computer-readable medium of claim 36, further comprising:
    program code for receiving a third temperature measure associated with a third point on a surface of the skin;
    program code for determining a second difference between the second temperature measure and the third temperature measure; and
    program code for generating an output signal indicating the presence of a blood vessel if the second difference exceeds a threshold.

38. The non-transitory computer-readable medium of claim 36, further comprising:
    program code for determining a direction of the blood vessel; and
    program code for generating an output signal indicating the direction of the blood vessel.

39. A non-transitory computer readable medium on which is encoded computer-executable program code, the program code comprising:
    program code for receiving a plurality of temperature measures, each of the plurality of temperature measures associated with a different location on a surface of a patient's skin from a temperature sensor disposed within a housing of a handheld device being moved across the patient's skin;
    program code for determining a difference between a pair of the plurality of temperature measures; and
    program code for generating an output signal indicating the presence of a blood vessel if the difference exceeds a threshold.

40. A system comprising:
    a housing;
    a temperature sensor disposed within the housing and operable to output a temperature measure of a location on a surface of a patient's skin; and
    a processor in communication with the temperature sensor and configured to:
        receive a first temperature measure at a first location from the temperature sensor,
        receive a second temperature measure at a second location from the temperature sensor, the second location different from the first location,
        determine a difference between the first temperature measure and the second temperature measure, and
        generate an output signal indicating the presence of a blood vessel if the difference exceeds a threshold.

41. A non-transitory computer-readable medium on which is encoded computer-executable program code, the program code comprising:
    program code for receiving a first temperature measure associated with a first location on a surface of a patient's skin, the first temperature measure generated by a temperature sensor;
    program code for receiving a second temperature measure associated with a second location on the surface of the skin, the second temperature measure generated by the temperature sensor;
    program code for determining a difference between the first temperature measure and the second temperature measure; and
    program code for generating an output signal indicating the presence of a blood vessel if the difference exceeds a threshold.

* * * * *